(12) United States Patent
Farahmand et al.

(10) Patent No.: US 10,292,691 B2
(45) Date of Patent: May 21, 2019

(54) MINIMALLY INVASIVE HEART STABILIZER

(71) Applicant: Sina Robotics and Medical Innovators Co. Ltd., Tehran (IR)

(72) Inventors: Farzam Farahmand, Tehran (IR); Arvin Houshmand, Tehran (IR); Alireza Mirbagheri, Tehran (IR); Saeed Mansouri, Isfahan (IR)

(*) Notice: Subject to any disclaimer, the term of this patent is extended or adjusted under 35 U.S.C. 154(b) by 161 days.

(21) Appl. No.: 15/420,047

(22) Filed: Jan. 30, 2017

(65) Prior Publication Data

US 2017/0189003 A1 Jul. 6, 2017

Related U.S. Application Data

(60) Provisional application No. 62/288,456, filed on Jan. 29, 2016.

(51) Int. Cl.
*A61B 17/02* (2006.01)
*A61B 17/34* (2006.01)
*A61B 17/00* (2006.01)
*A61B 17/29* (2006.01)
*A61B 17/30* (2006.01)
*A61B 90/00* (2016.01)

(52) U.S. Cl.
CPC .......... *A61B 17/02* (2013.01); *A61B 17/0218* (2013.01); *A61B 17/3423* (2013.01); *A61B 2017/00243* (2013.01); *A61B 2017/00703* (2013.01); *A61B 2017/0243* (2013.01); *A61B 2017/2927* (2013.01); *A61B 2017/2929* (2013.01); *A61B 2017/2938* (2013.01); *A61B 2017/306* (2013.01); *A61B 2090/067* (2016.02)

(58) Field of Classification Search
CPC ............ A61B 17/0206; A61B 17/0218; A61B 2017/0243
See application file for complete search history.

(56) References Cited

U.S. PATENT DOCUMENTS

| | | | |
|---|---|---|---|
| 5,836,311 A | * | 11/1998 | Borst ...................... A61B 17/02 128/897 |
| 7,250,028 B2 | | 7/2007 | Julian et al. |
| 8,460,172 B2 | | 6/2013 | Meyer et al. |
| 2001/0023311 A1 | * | 9/2001 | Snow ...................... A61B 17/02 600/37 |
| 2012/0157788 A1 | | 6/2012 | Serowski et al. |

* cited by examiner

*Primary Examiner* — Carrie R Dorna
(74) *Attorney, Agent, or Firm* — Bajwa IP Law Firm; Haris Zaheer Bajwa (57) ABSTRACT

A minimally invasive heart stabilizer includes a guide tube, a revolute joint, a stabilizing end-effector, and a linkage. The guide tube is sized to allow insertion through an endoscopic cannula. The revolute joint is coupled to a distal end of the guide tube. The stabilizing end-effector is coupled to the revolute joint. The linkage has a distal end and a proximal end. The distal end is pivotally connected to the end-effector. The stabilizing end-effector includes two tissue engaging members in parallel alignment with one another. The two tissue engaging members are joined via an arrangement of links.

8 Claims, 7 Drawing Sheets

MINIMALLY INVASIVE HEART STABILIZER

CROSS REFERENCE TO RELATED APPLICATION

This application claims the benefit of priority from U.S. Provisional Patent Application Ser. No. 62/288,456, filed on Jan. 29, 2016, and entitled "A MINIMAL INVASIVE HEART STABILIZER," which is incorporated herein by reference in its entirety.

TECHNICAL FIELD

The present disclosure generally relates to the field of minimally invasive surgery, particularly to minimally invasive surgical instruments, and more particularly to a minimally invasive heart stabilizer.

BACKGROUND

In order to remove a severe blockage of a coronary artery, an open heart surgery may be performed by splitting the sternum and forcing the chest cavity open to access the heart of a patient. Due to the trauma that may be created to the patient as a result of splitting the sternum and opening the chest cavity, there is a need in the art for systems and methods for performing minimally invasive heart surgeries. In a minimally invasive heart surgery, the surgical instruments may be inserted into a patient's body through small incisions on the chest. As a result, the trauma and prolonged recovery of an open heart surgery may be avoided.

In order to perform a coronary procedure without stopping the heart, the heart needs to be stabilized. A heart stabilizer is utilized during the procedure to limit the movements of the heart at the surgical site. In a minimally invasive heart surgery, the heart stabilizer needs to be capable of being inserted through a small incision and it needs to have the required maneuverability within the chest cavity of a patient. Consequently, there is a need in the art for a heart stabilizer that may be used in a minimally invasive heart surgery.

SUMMARY

In one general aspect, the present disclosure describes a minimally invasive heart stabilizer that may include a guide tube that may be sized to allow insertion through an endoscopic access cannula; a revolute joint that may be connected with the distal end of the guide tube; and a stabilizing end-effector that may be connected with the revolute joint.

In one implementation, the stabilizing end-effector may include at least two tissue engaging members in parallel alignment with one another and the tissue engaging members may be joined with one another via an arrangement of links. The arrangement of links may be configured to urge, upon actuation by a first actuating rod, the tissue engaging members to move toward one another in a closed position or away from one another in an open position while maintaining their parallel alignment.

According to an implementation, each tissue engaging member may include at least one suction port that may be configured to apply suction to a target tissue during stabilization.

According to other implementations, the stabilizer may further include a linkage. The distal end of the linkage may be pivotally connected to the end-effector and the proximal end of the linkage may be pivotally connected with a second actuating rod disposed within the guide tube. The second actuating rod and the linkage may be configured to urge the stabilizing end-effector to pivot about the revolute joint to a straight arrangement with respect to the guide tube upon actuation by a second manipulating rod.

According to some implementations, the arrangement of links may include: at least two connecting links that may be configured to receive respective tissue engaging members therein; at least two first links; at least two second links; at least two third links; a main link; and a sliding link configured to be slidably movable on the main link. The distal end of each first link may be connected with a location near the distal end of a respective connecting link by a pin joint and the proximal end of each first link may be connected with the distal end of the main link by a pin joint. The distal end of each second link may be connected with the proximal end of a respective connecting link by a pin joint and the proximal end of each second link may be connected with a location near the distal end of the main link by a pin joint. The distal end of each third link may be connected with a location between the proximal and the distal ends of each second link by a pin joint and the proximal end of each third link may be connected with the sliding link by a pin joint.

According to some implementations, the sliding link may be coupled with the first actuating rod. The sliding link may be configured to slide on the main link on a sliding path upon actuation by the first actuating rod. A forward movement of the sliding link toward the distal end of the main link may urge the connecting links toward one another via the first and second links, thereby urging the at least two tissue engaging members to move toward one another in a closed position.

According to an implementation, the sliding path may be defined by a stopper attached to the main link in the proximal third of the main link and a seat attached to the distal third of the main link.

According to an implementation, the distal end of the linkages is pivotally connected to the end-effector via pivotally connecting the distal end of the linkage with the stopper.

According to some implementations, the stabilizer may further include a measuring device coupled with the revolute joint, and the measuring device may be configured to measure the amount of rotational movement of the main link about the pivot point.

According to some implementations, the proximal end of the linkage may be pivotally connected with the second actuating rod by pivotally coupling the proximal end of the linkage with a distal attachment member disposed within the guide tube. The distal attachment member may be attached to the distal end of the actuating rod, where the distal attachment member may be linearly movable along the longitudinal axis of the guide tube upon actuation by the actuating rod.

According to an implementation, the at least one suction port of each tissue engaging member may be in fluid communication with a source of vacuum to apply suction to the target tissue.

According to another general aspect, the present disclosure describe a method for stabilizing a surgical site during a minimally invasive heart surgery. The method may include the steps of: attaching a stabilizing end-effector to a surgical site located on a surface of a beating heart; pivotally connecting the stabilizing end-effector with a revolute joint that may only allow the stabilizing end-effector to move along a normal direction of the surgical site; connecting the revolute joint with a distal end of a guide tube that may be an elongated tube capable of being inserted into a chest cavity of a patient; and fixing a proximal end of the guide tube by a fixing mechanism outside the chest cavity of the patient.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

In a minimally invasive surgery, for example a minimally invasive heart surgery, incisions may be made on a patient's body and access sheaths or cannulas may be placed inside the incisions. Surgical instruments may be introduced into the patient's body via the access cannulas. During a procedure such as a minimally invasive coronary artery bypass graft, the surgical site surrounding the coronary artery is in motion due to the beating of the heart. Heart stabilizers are generally used in beating heart surgeries to stabilize the surgical site on the beating heart. The stabilizers usually stabilize the surgical site in all directions meaning they limit the movement of the heart at the surgical site.

Disclosed herein is a minimally invasive stabilizer that may be configured to inhibit such motion by engaging the surface of the heart. The minimally invasive stabilizer of the present disclosure may be utilized to inhibit the motion of the surgical site in at least one direction. The stabilizer of this invention is designed with a revolute joint that allows a vertical movement of its end-effector along the normal axis of the surgical site. This new design allows a free movement of the heart along the normal axis of the surgical site. The purpose of designing a stabilizer that limits the movements of the heart at the surgical site in all directions but the normal direction may include avoiding exerting unnecessary pressure to the surface of the heart. Moreover, the new design allows for measuring the movement of the heart in the normal direction, which may then be fed to a slave robotic arm as a feedback, the robotic arm may use the feedback to synch its movement with the beating of the heart along the normal axis of the surgical site.

With this overview, reference is now made to the drawings to more fully describe the minimally invasive stabilizer of the instant application.

Figure 1:
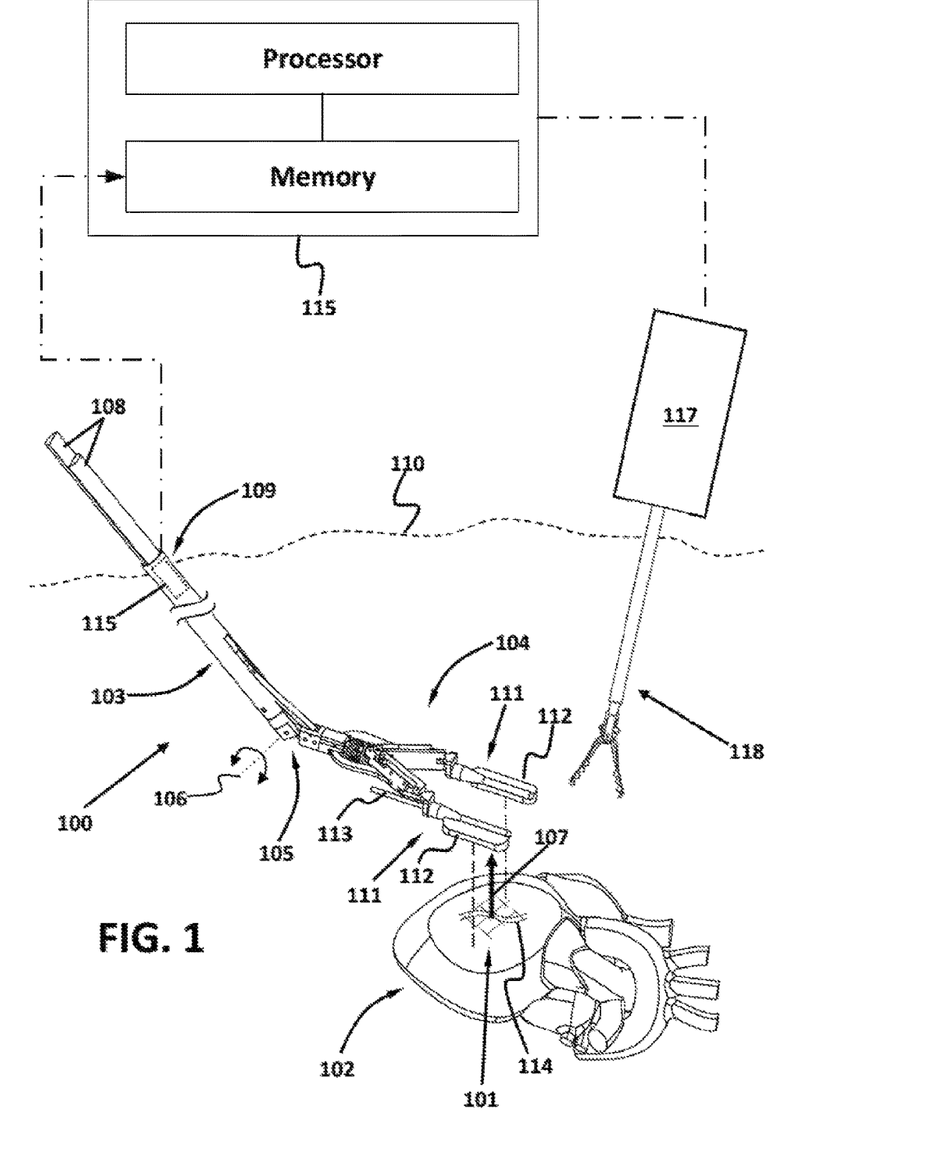
FIG. 1 shows an implementation of a minimally invasive stabilizer, according to one or more aspects of the present disclosure.

FIG. 1 shows an implementation of a minimally invasive stabilizer 100 that may be utilized to stabilize a surgical site 101 on a beating heart 102. According to one or more aspects of the present disclosure, the stabilizer 100 may include a narrow elongated guide tube 103 that may be connected from its distal end with a stabilizing end-effector 104 via a revolute joint 105. The revolute joint 105 may provide a single-axis rotation function that may allow the stabilizing end-effector 104 to pivot about a single axis 106 at the distal end of the guide tube 103. The single axis 106 may be perpendicular with a normal axis 107 of the surgical site 101. As will be described later in this disclosure, the stabilizing end-effector 104 may be actuated and locked in a deployment or closed position (not shown in FIG. 1) by one or more actuating rods 108. The stabilizer 100 may be introduced into a patient's body via an incision 109 made on a body wall 110, for example the chest wall, while the end-effector 104 is in its deployment position. Then the actuating rods 108 may be utilized to release the end-effector 104 from its deployment position to its active or opened position, as shown in FIG. 1.

Referring to FIG. 1, the end-effector 104 may include at least two stabilizing bodies 111 each having at least one tissue engaging member 112. Each tissue engaging member 112 may have an opening that may be in fluid communication with a rigid tube 113. The rigid tube 113 may be connected to a flexible tube (not shown in FIG. 1). The flexible tube may be connected to a source of vacuum to provide suction through the opening on the tissue engaging member 112. Such suction holds the stabilizer 100 in firm contact with the surgical site 101. The end-effector 104 may be positioned with one tissue engaging member 112 on either side of a coronary artery or any vessel of interest 114, thereby the stabilizer 100 may prevent or limit the motion of the surgical site 101 surrounding the vessel of interest 114 in at least one direction.

With further reference to FIG. 1, the revolute joint 105 may be configured to allow for rotational movement of the end-effector 104 with respect to the guide tube 103 about the single axis 106 perpendicular to the normal direction 107 of the surgical site 101 and consequently the end-effector 104 may move up and down along the normal axis 107 of the surgical site 101. Benefits from this feature may include but are not limited to allowing the heart 102 to beat freely in normal direction 107; tracking the movement of the heart 102 in the normal direction 107 by tracking the rotational movement of the end-effector 104 about the revolute joint 105 by for example, an encoder 115. The data regarding the tracked motion of the heart 102 may be sent to a master controller 115 and the controller 115 may send feedback to a slave robotic arm 117 that may be manipulating a surgical tool 118 inside the chest cavity of the patient. The master controller 115 may accommodate the tracked motion of the heart 102 to maintain the alignment between the surgical tool 118 and the surgical site 101 during the surgery.

Stabilizing End-Effector

Figure 2A:
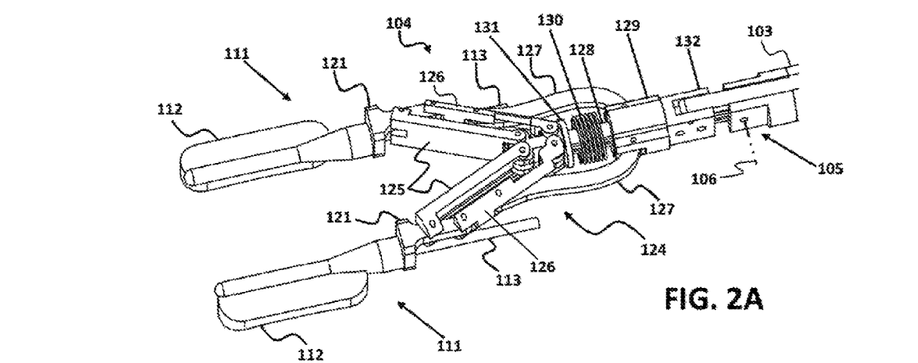
FIG. 2A shows a perspective view of the stabilizing end-effector, according to exemplary implementations of the present disclosure.
Figure 2B:
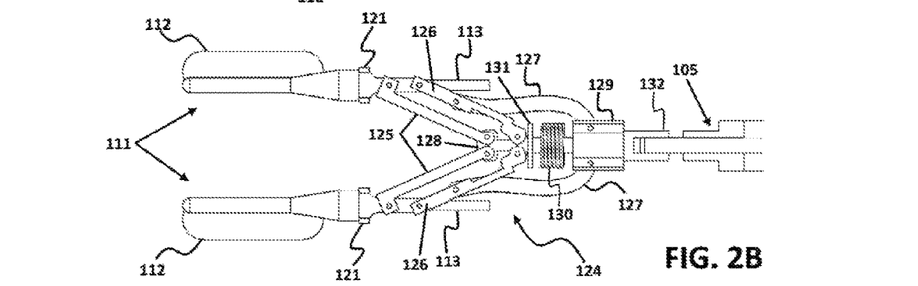
FIG. 2B shows a top view of the stabilizing end-effector, according to exemplary implementations of the present disclosure.
Figure 2C:
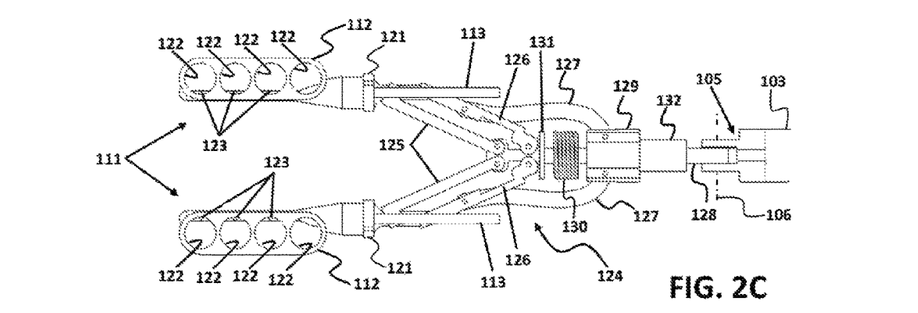
FIG. 2C shows a bottom view of the stabilizing end-effector, according to exemplary implementations of the present disclosure.

FIGS. 2A-2C illustrate an implementation of stabilizing end-effector 104 of the minimally invasive stabilizer 100 of FIG. 1. End-effector 104 may include at least two stabilizing bodies 111 each having at least one tissue engaging member 112. Each tissue engaging member 112 may be connected with a rigid tube 113. In an implementation, each tissue engaging member 112 and rigid tube 113 may be formed as a single piece that may be receivable inside a through hole on a connecting link 121.

FIG. 2B shows a top view of the stabilizing end-effector 104 and FIG. 2C shows a bottom view of the stabilizing end-effector 104 showing the underside of the tissue engaging members 112.

Referring to FIG. 2C, the underside of each tissue engaging member 112 may include at least one suction port 122. In the implementation shown in FIG. 2C, each tissue engaging member 112 includes four suction ports 122. Each rigid suction tube 113 may include a number of suction holes 123 thereon. The suction holes 123 may be aligned with the suction ports 122. Each rigid suction tube 113 may be connected to a vacuum source via a flexible tube and suction may be provided through the suction holes 123 along each tissue engaging member 112. Such suction through the suction ports 122 may hold the end-effector 104 in a firm contact with a target tissue in the surgical site 101 (visible in FIG. 1).

With continuing reference to FIGS. 2A-2C, the stabilizing bodies 111 may be joined with one another via an arrangement of links 124. The arrangement of links 124 may include the connecting links 121, first links 125, second links 126, third links 127, and a main link 128. The main link 128 may be pivotally connected with the revolute joint 105 and it may pivot about axis 106 with respect to the guide tube 103. Each stabilizing body 111 may be receivable within a through hole on a respective connecting link 121. Each connecting link 121 may be connected from a first location near its distal end to a distal end of a respective first link 125 by a pin joint and each connecting link 121 may be connected from its proximal end to a respective second link 126 by a pin joint at the distal end of the respective second link 126. The proximal end of each first link 125 may be connected with the main link 128 by a pin joint at the distal end of the main link 128. The proximal end of each second link 126 may be connected with a location near the distal end of the main link 128 by a pin joint. The distal end of each third link 127 may be connected with a respective second link 126 by a pin joint and the proximal end of each third link 127 may be connected with a sliding link 129. The sliding link 129 may be mounted on the main link 128 and it may be configured to be slidably movable on the main link 128 on a sliding path defined by a spring 130 and its corresponding seat 131 from one end and a stopper 132 from the other end. The stopper 132 may be fixed on the proximal third of the main link 128 and the seat 131 may be attached to the distal third of the main link 128.

Figure 3A:
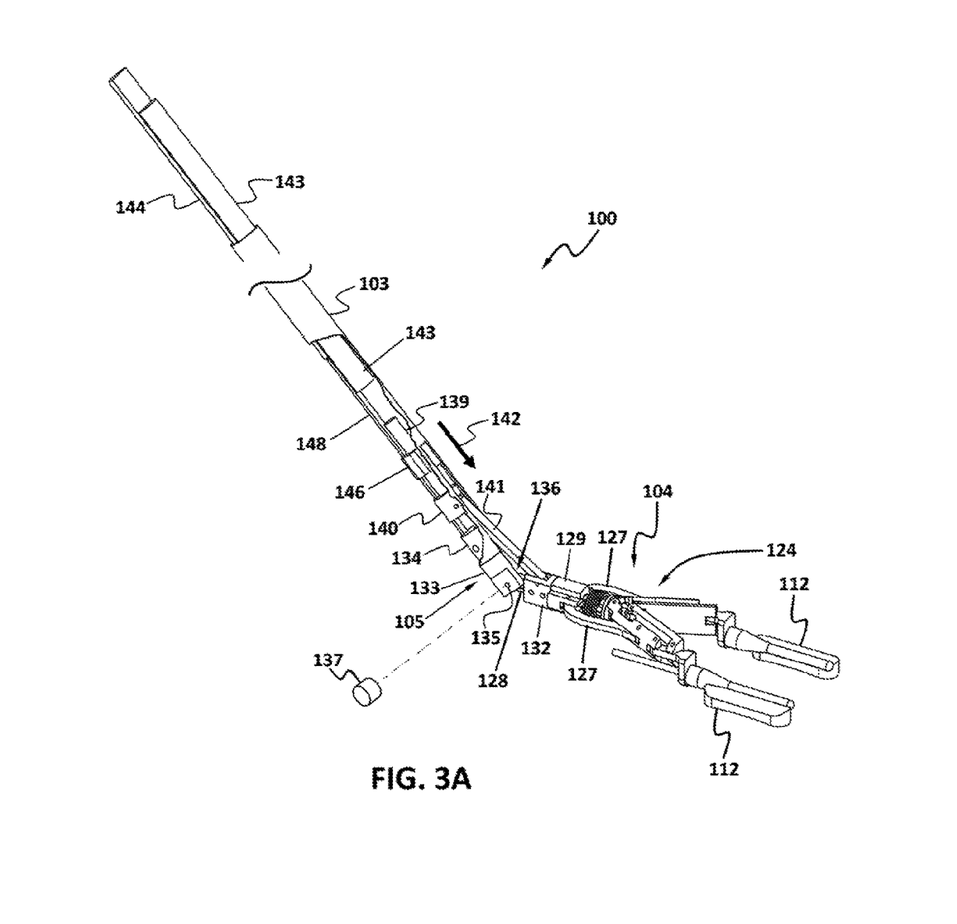
FIG. 3A shows an implementation of a minimally invasive stabilizer in its opened position, according to one or more aspects of the present disclosure.

Referring to FIG. 3A, the revolute joint 105 may be structure with two sections, namely, a joint section 133 and a connecting section 134. The joint section 133 may be configured to form a revolute joint or a single-axis joint with the main link 128. The joint section 133 may be connected with the main link 128 with a pin joint that allows the main link 128 to pivot about a pivot point 135 created by the joint section 133 with respect to the guide tube 103. The connecting section 134 that may be attached to the joint section 133 or alternatively it may be integrally formed with the joint section 133 may be configured as a cylindrical member with a diameter smaller than that of the guide tube 103 such that it can be fitted in place inside the distal end of the guide tube 103. The connecting section 134 may be attached and fixed to the distal end of the guide tube 103 by using a fastening means, such as a pin or a screw. The joint section 133 may have a slit formed thereon to allow the rotational movement of the main link 128 about pivot point 135.

Active or Opened Position of the Stabilizing End-Effector

FIG. 3A illustrates the end-effector 104 in its active or open position. In the active or opened position, the tissue engaging members 112 are parallel and spaced apart to allow surgical access to the surface of the heart between them. Moreover, in the active or open position, the main link 128 is free to pivot about the pivot point 135 defined by the revolute joint 105 with respect to the guide tube 103, as a result, the end-effector 104 may freely move up and down along the normal axis 107 (visible in FIG. 1) of the surface of the beating heart, on which the end-effector 104 is attached.

With further reference to FIG. 3A, in some implementations, a measuring device 137 may be coupled with the revolute joint 105. Device 137 may be configured to measure the rotational movement of the main link 128 of the end-effector 104 with respect to the guide tube 103. Device 137 may be, for example, an encoder, a potentiometer, or alternatively a strain gauge. The measuring device 137 may be configured to provide an exemplary implementation of the encoder 115 of FIG. 1.

Deployment or Closed Position of the End-Effector

Figure 3B:
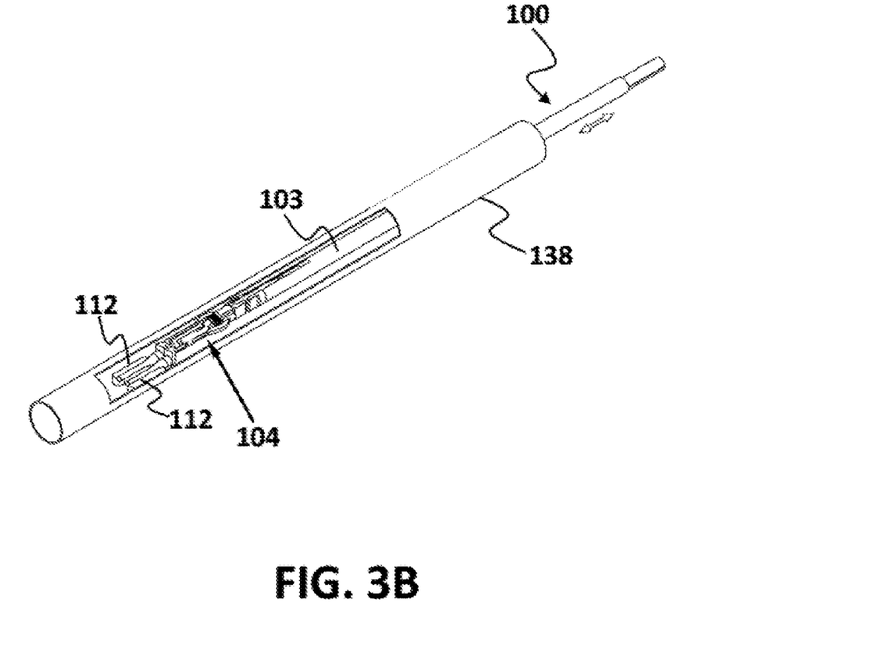
FIG. 3B shows an implementation of a minimally invasive stabilizer in its closed position, according to one or more aspects of the present disclosure.

Referring to FIG. 3B, in order to perform a minimally invasive heart surgery, the stabilizer 100 may be inserted into a patient's chest cavity through, for example an endoscopic access cannula 138. The guide tube 103 of the stabilizer 100 may be sized to allow insertion through the endoscopic access cannula 138. During the insertion, the stabilizing end-effector 104 must be in its deployment or closed position as shown in FIG. 3B.

Referring to FIG. 3B, in the deployment or closed position of the end-effector 104, the tissue engaging members 112 are parallel and are moved close toward one another, such that the end-effector 104 may be fit inside the endoscopic access cannula 138. Moreover, in the deployment position, the end-effector 104 and the guide tube 103 may be kept in a straight alignment along the longitudinal axis of the guide tube 103.

Referring to FIG. 3A, the minimally invasive stabilizer 100 may include a second actuating rod 139 that may be configured to urge the stabilizing end-effector 104 to pivot about the revolute joint 105 into a straight position with respect to the guide tube 103, such that the longitudinal axis of the end-effector 104 may be aligned with the longitudinal axis of the guide tube 103.

According to some implementations, the second actuating rod 139 may be attached from its distal end to a distal attachment member 140; and a linkage 141 that may be connected from its proximal end with the distal attachment member 140 by a pin joint and from its distal end with the stopper 132. The second actuating rod 139 and its distal attachment member 140 may be slidably movable within the guide tube 103. As the second actuating rod 139 moves towards the distal end of the guide tube 103 in the direction shown by arrow 142, it moves the distal attachment member 140 forward and as a result, the linkage 141 urges the stopper 132 to force the main link 128 of the end-effector 104 to pivot about the pivot point 135 into an aligned position with respect to the guide tube 103. According to an implementation, the stabilizer 100 may further include a guiding member 146 disposed within the guide tube 103 that may be structured to allow the second actuating rod 139 to pass through a hole thereon in order to guide the second actuating rod 139 along a straight pathway inside the guide tube 103.

According to an implementation, a second manipulating rod 143 may be provided in order to enable a user (i.e., a doctor or a surgeon) to push the second actuating rod 139 forward to align the end-effector 104 and the guide tube 103. The second manipulating rod 143 may be disposed within the guide tube 103 and it may be utilized to push the second actuating rod 139 forward in the direction shown by arrow 142.

Figure 4A:
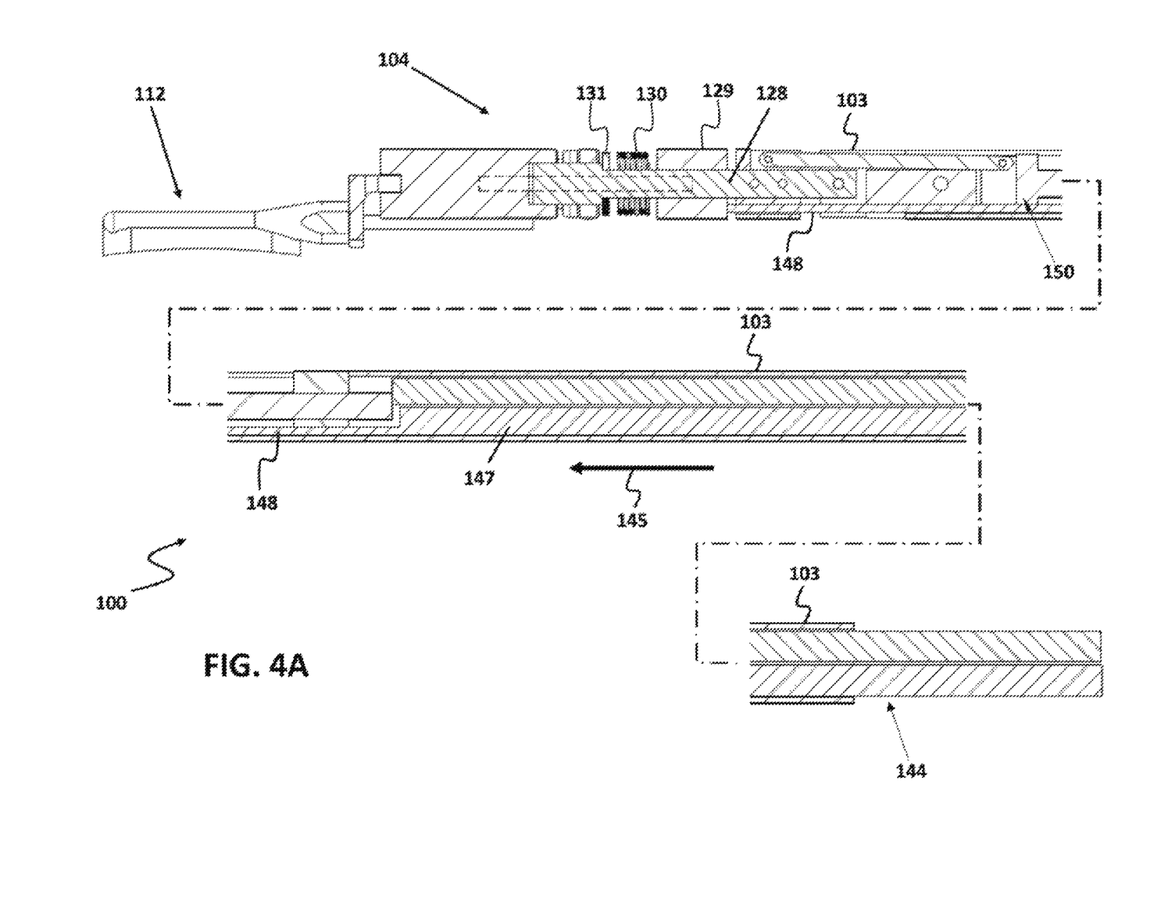
FIGS. 4A and 4B illustrate sectional left views of a minimally invasive stabilizer, according to one or more exemplary implementations of the present disclosure.

FIG. 4A illustrates a sectional left view of an exemplary minimally invasive stabilizer 100 in its deployment position. In the implementation shown in FIG. 4A, the end-effector 104 and the guide tube 103 are in a straight alignment along the longitudinal axis of the guide tube 103 and the tissue engaging members 112 are kept in a closed position, i.e., they are moved toward one another. The stabilizer 100 may further include a first manipulating rod 144 that may be disposed within the guide tube 103 and may be configured to be manipulated by a user. The user may push in the first manipulating rod 104 to close the tissue engaging members 112 or alternatively the user may pull out the first manipulating rod 144 to open the tissue engaging members 112. As used herein, closing the tissue engaging members 112 means moving the tissue engaging members 112 towards one another such that they may fit inside a cannula and opening the tissue engaging members 112 means moving the tissue engaging members 112 apart from one another to allow surgical access to the surface of the heart between them.

Referring to FIGS. 3A and 4A, in an implementation, the first manipulating rod 144 may be pushed in the direction shown by arrow 145. As the first manipulating rod 144 moves forward, it may urge the sliding link 129 to slide on the main link 128 towards the spring 130 and seat 131. As the sliding link 129 moves towards the seat 131, it may force the third links 127 to move forward. As the third links 127 move forward, they may urge the second links 126 to pivot such that their distal ends move toward one another and then the first links 125 may follow the movement of the second links 126 and their distal ends may move toward one another as well, thereby urging the two tissue engaging members 112 to move toward one another while maintaining their parallel alignment. Once the first manipulating rod 144 is pulled backwards, the spring 130 may restore the position of the sliding link 129 toward the stopper 132 and as a result the tissue engaging members 112 may move away from one another in an open position, while maintaining their parallel alignment.

Figure 4B:
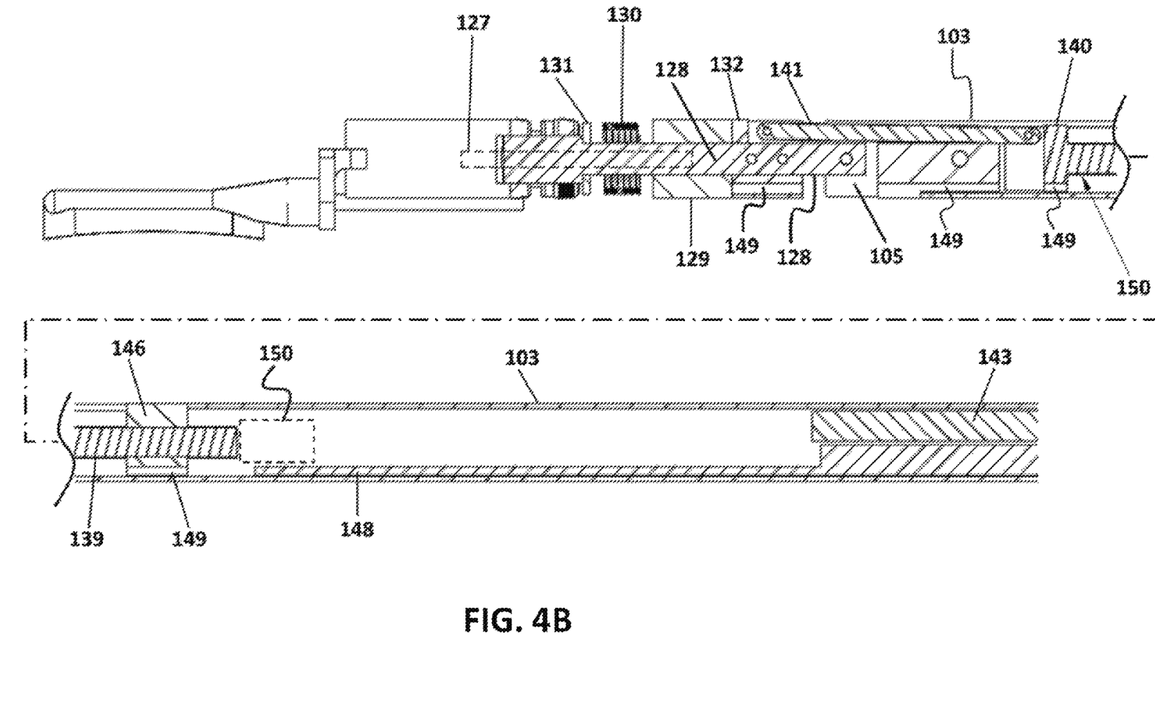

Referring to FIGS. 4A and 4B, the first manipulating rod 144 may include a larger section 147 and a smaller section 148. As the first manipulating rod 144 is pushed forward, the smaller section may pass through holes that may be provided in the guiding member 146, the distal attachment member 140, the revolute joint 105, and the stopper 132. These holes that are labeled with the reference numeral 149 in FIG. 4B may define the pathway along which the smaller section 148 of the first manipulating rod 144 may be pushed forward to urge the sliding link 129 to move forward.

Deployment of the Minimally Invasive Stabilizer

Referring to FIGS. 4A and 4B, according to some implementations, in order to deploy the stabilizer 100 into a patient's body through a cannula, the following steps may be taken: the second actuating rod 139 may be used to force the end-effector 104 to pivot about the revolute joint 105 into a straight alignment with respect to the guide tube 103; and then the first manipulating rod 144 may be pushed in to force the tissue engaging members 112 to a closed position. As a result, the stabilizer 100 may fit inside a cannula and it can be inserted into the patient's body.

Referring to FIG. 3A, after the deployment, the first manipulating rod 144 may be pulled out by the user to open the tissue engaging members 112 and then the second manipulating rod 143 may be released to allow the end-effector 104 to freely pivot about the pivot point 135 defined by the revolute joint 105.

In an aspect, the present disclosure describes a method for stabilizing a surgical site during a minimally invasive heart surgery, such that the movements of the surgical site may be inhibited in all directions except the normal direction of the surgical site. Furthermore, the present disclosure describes a method for stabilizing a surgical site during a minimally invasive heart surgery, such that the movements of the heart along the normal axis of the surgical site may be tracked or optionally be smoothed. Smoothing the motions of the heart in the normal direction of the surgical site, as used herein, may include but is not limited to removing the high frequency motions of the heart in the normal direction of the surgical site.

Referring to FIG. 4B, the second actuating rod 139 may be coupled with a smoothing device 150 that may be configured to smooth the motions of the heart in the normal direction of the surgical site. According to some implementations, the smoothing device 150 may be a force actuator, such as a spring and a damper or it may be an electrical, hydraulic or pneumatic system that may be configured to remove the high frequency motions of the heart in the normal direction of the surgical site.

Figure 5:
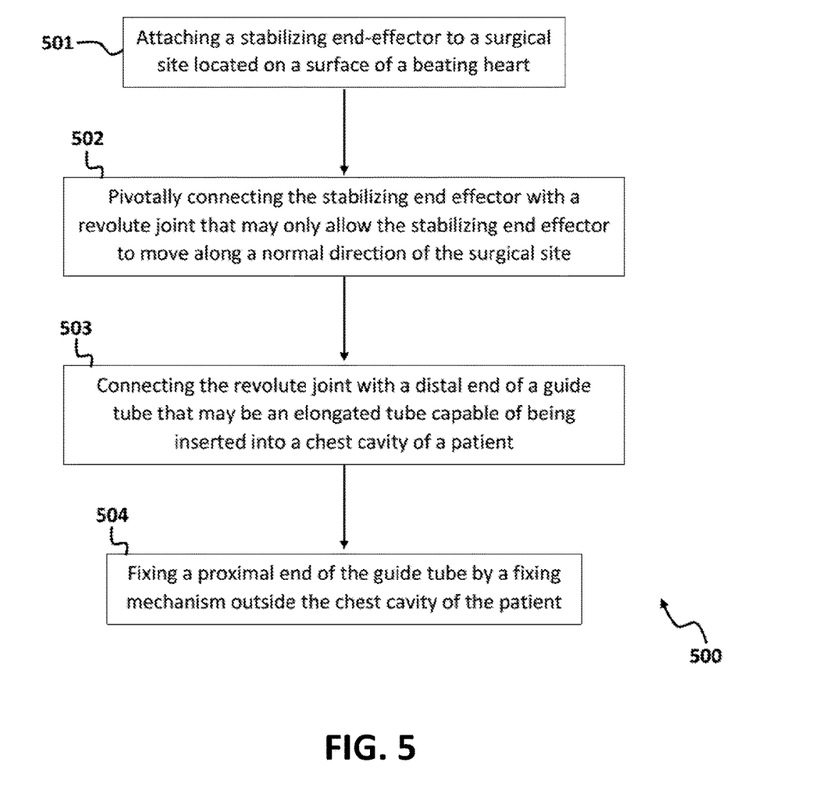
FIG. 5 shows a block diagram of an exemplary method for stabilizing a surgical site during a minimally invasive heart surgery.

FIG. 5 shows a block diagram of an exemplary method 500 for stabilizing a surgical site during a minimally invasive heart surgery that may include the steps of: attaching a stabilizing end-effector to a surgical site located on a surface of a beating heart (step 501); pivotally connecting the stabilizing end-effector with a revolute joint that may only allow the stabilizing end-effector to move along a normal direction of the surgical site (step 502); connecting the revolute joint with a distal end of a guide tube that may be an elongated tube capable of being inserted into a chest cavity of a patient (step 503); and fixing a proximal end of the guide tube by a fixing mechanism outside the chest cavity of the patient (step 504).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A minimally invasive heart stabilizer, comprising:
a guide tube;
a revolute joint coupled to a distal end of the guide tube;
a stabilizing end-effector coupled to the revolute joint, the stabilizing end-effector comprising two tissue engaging members in parallel alignment with one another, each tissue engaging member of the tissue engaging members including at least one suction port in fluid communication with a source of vacuum, each tissue engaging member configured to engage a target tissue by applying suction to the target tissue via the at least one suction port;
a linkage having a distal end and a proximal end, the distal end pivotally connected to the stabilizing end-effector, the proximal end pivotally connected to a second actuating rod disposed within the guide tube; and
an arrangement of links joining the two tissue engaging members, the arrangement of links comprising:
a main link;
a sliding link configured to slidably move on the main link;
two connecting links, each connecting link of the two connecting links configured to receive a respective tissue engaging member;
two first links, a distal end of each of the two first links connected with a location near a distal end of each of the connecting links by a pin joint and a proximal end of each of the two first links connected with a distal end of the main link by a pin joint;
two second links, a distal end of each of the two second links connected with the proximal end of each of the connecting links by a pin joint and a proximal end of each of the two second links connected with a location near the distal end of the main link by a pin joint; and
two third links, a distal end of each of the two third links is connected with a location between the proximal end and the distal end of each of the two second links by a pin joint and a proximal end of each of the two third links connected with the sliding link by a pin joint,
wherein the arrangement of links is configured to urge, upon actuation by a first actuating rod, the two tissue engaging members to move toward one another in a closed position or away from one another in an open position while the two tissue engaging members maintain their parallel alignment,
wherein the second actuating rod and the linkage are configured to cause the stabilizing end-effector to pivot about the revolute joint.

2. The stabilizer according to claim 1, wherein:
the sliding link is coupled with the first actuating rod,
the sliding link is configured to slide on the main link on a sliding path upon actuation by the first actuating rod,
a forward movement of the sliding link toward the distal end of the main link urges the connecting links toward one another via the two first and second links, thereby urging the two tissue engaging members to move toward one another in a closed position.

3. The stabilizer according to claim 2, wherein the sliding path is defined by a stopper coupled to a proximal end of the main link and a seat coupled to the distal end of the main link.

4. The stabilizer according to claim 3, wherein the distal end of the linkage is pivotally connected to the end-effector via pivotally connecting the distal end of the linkage with the stopper.

5. The stabilizer according to claim 1, wherein:
the main link is pivotally connected with the revolute joint,
the main link is configured to pivot about a pivot point defined by the revolute joint about an axis perpendicular with a longitudinal axis of the main link.

6. The stabilizer according to claim 1, wherein:
the proximal end of the linkage is pivotally connected with the second actuating rod by a pin join,
and
the second actuating rod is linearly movable along the longitudinal axis of the guide tube upon actuation by the first actuating rod.

7. The stabilizer according to claim 1, wherein each of the two tissue engaging members include a plurality of suction ports.

8. A minimally invasive heart stabilizer, comprising:
a guide tube;
a revolute joint coupled to a distal end of the guide tube;
a stabilizing end-effector coupled to the revolute joint, the stabilizing end-effector comprising:
  two suction ports in parallel alignment with one another, each suction port of the two suction ports configured to apply suction to a target tissue by being in fluid communication with a source of vacuum; and
  an arrangement of links configured to join the two suction ports, the arrangement of links comprising:
    a main link;
    a sliding link configured to slidably move on the main link;
    two connecting links, each connecting link of the two connecting links configured to receive a respective suction port;
    two first links, a distal end of each of the two first links connected with a location near a distal end of each of the connecting links by a pin joint and a proximal end of each of the two first links connected with a distal end of the main link by a pin joint;
    two second links, a distal end of each of the two second links connected with the proximal end of each of the connecting links by a pin joint and a proximal end of each of the two second links connected with a location near the distal end of the main link by a pin joint; and
    two third links, a distal end of each of the two third links connected with a location between the proximal end and the distal end of each of the two second links by a pin joint and a proximal end of each of the two third links connected with the sliding link by a pin joint, and
  wherein the arrangement of links is configured to urge, upon actuation by a first actuating rod, the two suction ports to move toward one another in a closed position or away from one another in an open position while the two suction ports maintaining their parallel alignment.

* * * * *